(12) United States Patent
Yvin et al.

(10) Patent No.: US 6,303,587 B1
(45) Date of Patent: Oct. 16, 2001

(54) COMPOSITION AND METHOD FOR STIMULATING POLLEN GERMINATION

(75) Inventors: Jean-Claude Yvin; Florence Levasseur, both of Saint Malo; Kiem-Ngoc Tran Thanh; Van le Bui, both of Gif sur Yvette, all of (FR)

(73) Assignee: Laboratoires Goemar S.A. (FR)

( * ) Notice: Subject to any disclaimer, the term of this patent is extended or adjusted under 35 U.S.C. 154(b) by 0 days.

(21) Appl. No.: 09/381,569

(22) PCT Filed: Mar. 19, 1998

(86) PCT No.: PCT/FR98/00555

§ 371 Date: Dec. 27, 1999

§ 102(e) Date: Dec. 27, 1999

(87) PCT Pub. No.: WO98/41091

PCT Pub. Date: Sep. 24, 1998

(30) Foreign Application Priority Data

Mar. 19, 1997 (FR) .................................. 97 03386

(51) Int. Cl.$^7$ .................................. A61K 31/70
(52) U.S. Cl. .................. 514/61; 514/53; 514/54
(58) Field of Search ................... 514/53, 54, 61

(56) References Cited

U.S. PATENT DOCUMENTS 5,284,818 * 2/1994 Shafer et al. ................ 504/115

FOREIGN PATENT DOCUMENTS

| 195 43 592 C1 | 2/1997 | (DE) . |
| 2 693 454 | 1/1994 | (FR) . |
| WO 90/02719 | 3/1990 | (WO) . |

OTHER PUBLICATIONS

Katiyar, S.R., et al. "Effects of carbohydrates on pollen germination and tube growth in *Pinus kesiya* Royle ex Gordon", Indian Biol. 22(1):1–4 (1990) Biological Abstracts, vol. 90 (1990) Philadelphia, PA, US, abstract No. 44536 (abstract only).

Goncalves, et al., "In vitro pollen germination of *Hevea camargoana*", Pesqui Agropecu Bras 17(2):287–292 (1982) Biological Abstracts, vol. 75 (1983) Philadelphia, PA, US, abstract No. 6126 (abstract only).

Biologie Vegetale, "Croissance Morphogenèse Reproduction", P. Champagnat, et al., see p. 1, lines 21–25 of specification for brief explanation.

* cited by examiner

*Primary Examiner*—Elli Peselev
(74) *Attorney, Agent, or Firm*—Kilpatrick Stockton LLP

(57) ABSTRACT

Composition for application, in particular to leaves, comprising an excipient, the conventional constituents of compositions for application, in particular to leaves, and an active ingredient, characterized by the fact that the active ingredient is constituted by at least one phytosanitary product capable of stimulating the germination of pollen grains, selected from the group comprising:

oligosaccharides having a degree of polymerization up to 10 and comprising up to 10, preferably up to 5 and, even more preferably, two glucidic units linked by β1-3, β1-4 et α1-3, particularly those of the group comprising laminaribiose, cellobiose, nigerose, laminaritriose, laminaritetraose and laminaripentaose, derivatives of the above oligosaccharides substituted on the free anomeric carbon atom or on all the carbon atoms having a free hydroxide by a radical selected from the group comprising:
$C_1$ to $C_5$ alkyl radicals, preferably the methyl radical,
$C_1$ to $C_5$ acyl radicals, preferably the acetyl radical,
aryl radicals, preferably pyridylamino radicals,
cycloalkyl radicals from $C_x$ to $C_y$,
amines,
the N-acetyl radical and
sulfate and phosphate radicals.

11 Claims, 1 Drawing Sheet

COMPOSITION AND METHOD FOR STIMULATING POLLEN GERMINATION

The invention concerns a composition comprising, as active ingredient at least one phytosanitary product of the type which can stimulate the germination of pollen grains.

It also concerns a process for the treatment of plants for the stimulation of the germination of pollen grains by application, in particular to leaves, of the said composition.

It concerns, finally, under the title of new industrial products, inasmuch as their use for the said stimulation is contemplated, the phytosanitary products which constitute the active ingredient of the said composition.

The germination of pollen grains occurs after pollinization during which the pollen grains are transported on the flowers and retained at the receptive surface of the stigma; this permits the fertilization as such and the constitution of the embryo due to the formation, originating from the pollen grain, of an organ called the pollen tube; this organ is embedded in the stigma, then in the style and finally penetrates up to the embryonic sac in which fertilization occurs.

It is well known, (see for example page 405 of BIOLOGIE VÉGÉTALE, *"Croissance Morphogenèse Reproduction"* by P. Champagnat, P. Ozenda and L. Baillaud, published by Masson & Cie, 1969) that the lifespan of the pollen grain, once pollinization occurs is short, and does not usually exceed a period of 24 hours.

And when the germination of a given pollen grain does not occur within this short period, the fertilization which it could have provoked does not occur and one of the possible descendants of the plant is lost.

The person skilled in the art has thus searched for methods for favoring the germination of pollen grains and thus increasing the yield of crops.

Thus, it has already been proposed to stimulate the germination of pollen grains by applying borate solutions to crops.

It has been found that the recorded results are not considered to be satisfactory by the users.

It has further been noted that saccharose which is the most abundant sugar in plants can to a certain extent stimulate the germination of pollen grains; in view of the poor results, the research leading to this finding has never exceeded the laboratory stage.

The invention thus aims to remedy this situation and to supply phytosanitary products of the type in question which respond, in a satisfactory manner and in any case better than saccharose and borate solutions, to the various practical needs.

And the Applicant Company has found, due to its thorough research, that in a surprising and unexpected fashion, this aim could be attained by having recourse, as phytosanitary products of the type in question, to those of a group comprising certain oligosaccharides whose structure, which is different from that of saccharose, allowed even less to predict that they possessed the desired stimulating property since certain oligosaccharides having a structure very close to the representatives of said group have no activity on the germination of pollen grains.

It follows that the composition for application, in particular to leaves, according to the invention, comprises an excipient, the conventional components of compositions for in particular application to leaves and an active ingredient, is characterized by the fact that the active ingredient is constituted by at least one phytosanitary product capable of stimulating the germination of pollen grains, selected from the group comprising:

oligosaccharides having a degree of polymerization up to 10 and comprising up to 10, preferably up to 5 and, even more preferably, two glucidic units linked by $\beta$1-3, $\beta$1-4 and $\alpha$1-3, particularly those of the group comprising laminaribiose, cellobiose, nigerose, laminaritriose, laminaritetraose and laminaripentaose, derivatives of the above oligosaccharides substituted on the free anomeric carbon atom or on all the carbon atoms having a free hydroxide by a radical selected from the group comprising:

$C_1$ to $C_5$ alkyl radicals, preferably the methyl radical,
$C_1$ to $C_5$ acyl radicals, preferably the acetyl radical,
aryl radicals, preferably pyridylamino radicals,
cycloalkyl radicals from $C_x$ to $C_y$,
amines,
the N-acetyl radical and
sulfate and phosphate radicals.

The process for the treatment of plants for the stimulation of the germination of pollen grains is characterized by the fact that it comprises the application, in particular to leaves, of the composition according to the invention.

According to an advantageous embodiment of the composition according to the invention, it comprises, in combination with the active ingredient constituted by the phytosanitary product capable of stimulating the germination of pollen grains, at least one other phytosanitary product, in particular a fungicide.

The invention will be better understood with the help of the further description which follows and the non limitative examples which are provided with respect to the advantageous embodiments.

Proposing, consequently, to stimulate the germination of pollen grains, the method below or an equivalent method is followed.

The plants to be stimulated are treated with a composition for application, in particular to leaves, comprising in addition to excipients and conventional constituents of such compositions, at least one of the phytosanitary products capable of stimulating the germination of said pollen grains and selected from the group as defined above.

This treatment is performed at the time of flowering, more specifically at the time of pollinization.

It is performed, preferably, before or at the moment of opening of the anthers.

It may be performed by spraying of the composition according to the invention.

It is possible to use a single spraying; however, it may be advantageous to renew this operation at least once; in this case, the first spraying is advantageously performed two days before the opening of the anthers and the second on the very day of opening.

The specific moment will be selected as a function of the treated plant.

Said plant may be constituted by any plant of agricultural or ornamental interest for which the fertilization requires either a mechanism of cross-pollinization, (called allopollinization), or a mechanism of direct pollinization (called autopollinization) in which the pollen and the stigma belong to the same individual. The plants which are not concerned by the present invention are those having external flower envelopes which do not open and in which the pollinization is performed without the pollen being freed and germinating directly in the anther; this is the case for cleistogamic flowers.

Good results were obtained with plants as divers as tobacco, vegetable plants such as carrots, tomatoes, cauliflowers and potatoes, fruit trees such as apple, cherry and plum, oleaginous plants such as soya, sunflower and rapeseed, cereals such as corn, flowers such as lily.

The concentration of active ingredient in the compositions for leaf application according to the invention is from 1 to 20% by weight, preferably from 1.5 to 10% and even more preferably from 2 to 8% by weight.

The quantity of the composition applied by hectare is such that it brings to the acre 10 to 1000 g of active ingredient, preferably from 20 to 500 g and even more preferably from 50 to 250 g.

When the composition is liquid, the excipient is generally water.

It is, however, possible to use, in the place of water, an excipient selected from the group comprising mineral oils, vegetable oils, all liquid fats and alcohols, in particular propyleneglycol or glycerine.

The essential conventional components of the compositions according to the invention depend upon the active matter of the treated plants; they are generally selected from the group comprising solid bulking agents, solvents, surface active agents, dispersing agents and emulsifying agents.

When the compositions according to the invention are in the form of powders, the excipient is advantageously constituted by a bulking agent, in particular inorganic.

This bulking agent may be selected from the group comprising kaolin, finely dispersed clay and talc.

In the case of compositions in the form of powders, the conventional constituents are generally selected from the group comprising dextrans.

It should be noted that the compositions in the form of powders are diluted, at the moment of use, in an excipient constituted, in particular, by water.

The compositions according to the invention may take the form of liquid fertilizers based on at least one of the phytosanitary products of the group defined above, optionally in combination with one or more balancing oligo-elements which may be selected from the group comprising the salts of molybdenum and manganese.

Some examples of compositions according to the invention are indicated hereafter.

EXAMPLE 1

Composition for Agricultural Use Based on Laminaribiose

In this composition, laminaribiose is associated with oligo-elements in the form of liquid fertilizer.

For 1 kg by weight/weight, this composition is constituted by

| | |
|---|---|
| magnesium sulfate, 7H$_2$O | 0.3010 kg |
| manganese sulfate, 1H$_2$O | 0.0510 kg |
| zinc sulfate, 7H$_2$O | 0.1060 kg |
| laminaribiose | 0.0350 kg |
| Tween 80 | 0.0050 kg |
| water | 0.5020 kg |
| | 1.0000 kg |

This composition may be used at a dose of 3 liters/ha at the flowering stage on fruit trees.

EXAMPLE 2

Composition for Agricultural Use Based on Cellobiose and Nigerose

This composition is in the form of a liquid fertilizer containing the active ingredients in association with boron and molybdenum.

For 1 kg by weight/weight, this composition is constituted by

| | |
|---|---|
| boric acid | 0.150 kg |
| sodium molybdate | 0.005 kg |
| cellobiose | 0.030 kg |
| nigerose | 0.030 kg |
| water | 0.780 kg |
| sodium methyl paraben | 0.005 kg |
| | 1.000 kg |

This composition may be used at a dose of 3liters/ha at the moment of pollinization on apple trees.

EXAMPLE 3

Composition for Agricultural Use Based on Laminaribiose

This soluble composition is in powder form and contains the active material associated with boron and molybdenum.

For 1 kg by weight/weight, this composition is constituted by

| | |
|---|---|
| boric acid | 0.300 kg |
| sodium molybdate | 0.010 kg |
| laminaribiose | 0.170 kg |
| kaolin | 0.520 kg |
| | 1.000 kg |

This composition may be used after dilution in water at 10 g/l at a dose of 1 kg/ha at the time of flowering of vegetable plants.

EXAMPLE 4

Composition for Agricultural Use Based on Nigerose and a Fungicide 1 g of nigerose is dissolved in 699 g of water.

In this solution is suspended 300 g of fungicide of trademark Manganil 80 sold by the company Bourgeois under the N° APV 7000073; this fungicide contains 80% of active material constituted by manebe.

The suspension thus obtained has a nigerose content of 0.1% and a manebe content of 24%.

It can be applied to the surface of leaves by spraying after dilution in water at a concentration comprised between 0.1 and 50 ml/l.

The quantity applied is 5 l/ha.

This composition has a stimulating effect on fertilization simultaneously with fungicidal protection.

It is advantageously used against mildew of vines and tomatoes.

For greater ease of transport and storage, concentrates are advantageously prepared which, at the time of use, are diluted with the appropriate quantity of excipient to provide the composition ready for use.

The concentrates comprise all the constituents of the compositions according to the invention in the weight ratios of these constituents in the compositions as put to use; on the contrary, the exicpient is present only in a quantity compatible with the mode of spraying.

Oil based sprayable compositions or emulsifiable compositions, in particular in the case of mixtures with additional water insoluble substances can also be used.

Insofar as they are not available on the market, the active materials used in the compositions according to the invention are accessible by known reactions of enzymatic or acid degradation of substrates containing them.

By way of example, the preparations of cellobiose, laminaribiose and nigerose are described hereafter.

EXAMPLE 5

Preparation of cellobiose ($\beta$1-4-diglucose)

The raw material used is cellulose.

100 g of commercial cellulose, i.e. cellulose commercialized by the Company Fluka as "cellulose powder", after dissolution in 1000 ml $H_2O$ is reacted with an $\beta$(1-4)-glucanohydrolase or commercial cellulase, i.e. cellulase commercialised by Signa Chimie as EC 3.2.1.4.

The quantity of enzyme added is 1 g, i.e. 300 units.

The hydrolysis conditions are as follows:

pH:5 temperature: 37° C.

hydrolysis time: 5 hours.

After these 5 hours of incubation, the enzyme is inhibited by heating at 100° C. for 15 minutes.

The solution thus obtained is subjected to a tangential ultrafiltration on a system commercialized under the trademark PELLICON by the Company Millipore; this system is equipped with a cassette of a porosity of 1000 Daltons associated with a pump commercialized under the trademark PROCON by the Company Millipore.

The filtrate obtained is concentrated by evaporation under vacuum and then lyophilized; 50 g of powder corresponding to pure cellobiose is obtained; the purity of this cellobiose is verified by high pressure liquid chromatography, more particularly by ionic chromatography coupled with amperometry, using the ion exchange resin commercialised Dionex Chemical Corp., daughter company of Dow, under the trademark DIONEX.

EXAMPLE 6

Preparation of laminaribiose ($\beta$1-3-diglucose).

The raw material is curdlan, i.e. a polymer extracted from *Alcaligenes faecalis*.

100 g of curdlan commercialised under the reference C7821 by Sigma Chimie, after dissolution in 1000 ml water, is subjected to the action of a $\beta$-1-3-endoglucanase EC 3.2.1.2.1 commercialised under reference C4511 by Sigma Chimie.

The quantity of enzyme used is 1 g, i.e. 60 units.

The conditions of hydrolysis are as follows:

pH: 6 temperature: 40° C.

hydrolysis time: 6 hours.

After 6 hours of incubation, the enzymatic reaction is stopped by heating at 100° C. for 15 minutes.

The solution thus obtained is subjected to a tangential ultrafiltration on a system commercialized under the trademark PELLICON by the Company Millipore; this system is equipped with a cassette of a porosity of 1000 Daltons associated with a pump commercialized under the trademark PROCON by the Company Millipore.

The filtrate is then concentrated by reverse osmosis and then lyophilized and 70 g of powder constituted by glucose and laminaribiose in 50/50 proportions is obtained.

The laminaribiose is isolated by addition in the mixture of a yeast obtained from the strain *Shizosaccharomyces pombe* IFO 0358 which specifically metabolizes the glucose with no degradation of laminaribiose.

After elimination of the yeast cells, laminaribiose of a purity of 90% is obtained.

EXAMPLE 7

Preparation of nigerose ($\alpha$-1-3-diglucose).

The raw material is commercial nigeran.

100 g of nigeran commercialised under the reference N2888 by Sigma Chimie is subjected to the action of a solution of 0.1 M sulphuric acid at a temperature of about 80° C. for a period of 6 hours.

This hydrolysis is followed by a step of neutralization by addition of a strong base such as NaOH until a pH of between 6 and 8 is obtained, then a desalting step by passage of the neutralized product on an ion exchange resin and finally a step of reduction into powder by atomization.

70 g of powder containing about 35 g of nigerose mixed with 35 g of glucose is thus obtained.

The nigerose is isolated by passage of the nigerose+glucose mixture on a chromatography column filled with resin commercialised by Pharmacia under the trademark SEPHADEX G10.

Two separate fractions are obtained as a function of their molecular weights, i.e. on the one hand, glucose and, on the other, nigerose of a purity of 90%.

The other preferred oligosaccharides, i.e. laminaritriose, laminaritetraose and laminaripentaose may be prepared by application of the method of enzymatic degradation of $\beta$-1-3 glucans followed by purification, illustrated in example 6.

It is as a result of extensive selection research, rendered possible due to laboratory tests created in the context of this research and which will be described below, that the Applicant Company was able to identify the phytosanitary products which are used according to the invention in the compositions defined above.

These tests have also allowed the determination of the optimal concentrations of active ingredient in said compositions.

The results obtained have been verified by field tests.

The basis of the tests in question and which are themselves original, consists in germinating pollen grains of a given plant in an aqueous solution of the phytosanitary substance being tested from the viewpoint of its stimulating activity of germination.

It is important to ensure that the water in which these experiments are performed is of a very high purity; the minimum degree of purity may be characterized by a resistivity greater than 10 mega-$\Omega$×cm.

Said tests are described below in their application to a particular plant, i.e. tobacco.

Pollen grains from Nicotiana tabacum are harvested from just dehiscent anthers on well opened flowers; each flower has five anthers.

For this harvest, the anthers are detached from their filaments; four anthers are identical with respect to the length of the filament; the fifth which has a shorter filament is not used in order to preserve homogeneity.

For greater ease, the manipulations are performed under a binocular magnifying glass; the walls of the anthers are removed, after having been placed in a watch glass filled with water responding to the above conditions of purity, in order to liberate the pollen grains.

The pollen grains are cleaned by three or four washings with the same pure water.

The water is decanted and the grains which float are eliminated.

The excess water is eliminated and a suspension of pollen grains designated as "SP" containing about 100 pollen grains per ml of water is obtained.

Aqueous solutions of increasing concentrations of the products to be tested from the viewpoint of their possible stimulating activity on germination of pollen grains are also prepared; these increasing concentrations are of 5 µg/ml, 10 µg/ml, 50 µg/ml, 100 µg/ml, 500 µg/ml, 1000 µg/ml, 1500 µg/ml, 2000 µg/ml, 2500 µg/ml, 3000 µg/ml, 4000 µg/ml, 5000 µg/ml, 6000 µg/ml.

From a practical viewpoint titration plates comprising for example 6 rows of 4 wells having a diameter of 1 cm and a depth of 1 cm are used.

Instead of titration plates, Petri dishes may be used.

100 µl of a solution containing one of the products to be tested at one of the above concentrations is introduced into each well.

A volume of 100 µl of the suspension "SP" is also introduced into each well.

The mixture is homogenized.

It is within the wells of the titration plates that the germination of the pollen grains occurs and that the stimulating activity of the phytosanitary products is studied.

Each experiment is performed at least five times and each time with two repetitions for each product.

Advantageously, in a first approach, intermediate concentrations of 500 à 1000 µg/ml are tested and, in function of the results obtained, the field of the experiments is enlarged towards higher or lower concentrations.

Simultaneously, two control experiments are performed.

A first control is performed in water corresponding to the above conditions of purity, i.e. directly on the suspension "SP".

A second control is performed using a germination buffer comprising in water saccharose at 12% by weight, boric acid at 0.01% by weight, chloride of calcium dihydrate at 0.3% by weight, In this buffer, the saccharose is present at 12%; it is at this dose that saccharose was previously used in the known laboratory experiments; the buffer also contains the boron ion at a concentration corresponding to those at which it was used in borate compositions known for the stimulation of germination of pollen grains.

The titration plates are then maintained in the dark for a period of 24 to 48 hours at a temperature of 22° C. to 24° C.

A first observation is made under the binocular magnifying glass 5 to 6 hours, a second 24 hours and a third 36 hours after the start of the experiment.

At each of these observations a certain number of parameters is noted, i.e.:

the density of the germinating pollen grains, the length of the pollen tube, this measurement being facilitated by the use of a binocular magnifying glass having an internal standard, the intensity of agglutination of the pollen grains, and the lysis of these grains.

These parameters are not easily quantifiable, even for the length of the pollen tube given that they are not always straight.

A stimulation is considered as having occurred if the number of pollen tubes developed in the treated wells is greater than the number of tubes developed in the wells containing the control.

To translate the intensity of the stimulation observed for a tested product, it is agreed that when there is no stimulation, the activity is considered as being of 0%, when the stimulation is observed as total and complete germination of pollen grains, the activity is considered as being 100%, the intermediate activity values, expressed in %, correspond to stimulations which are observed as a germination of part of the pollen grains.

In the case of tobacco, the activity found for the phytosanitary products used in the compositions according to the invention and belonging to the preferred group defined above, as well as the optimal concentrations determined for these products, is given in Table A below in which the chemical composition of each of the products in question is also given.

TABLE A

| Phytosanitary product | Monosaccharidic composition | Bonds between monosaccharides | Activity | Optimal concentration (in µg/ml) |
|---|---|---|---|---|
| Laminaribiose | glucose-glucose | β 1-3 | 80% | 2000 |
| Cellobiose | glucose-glucose | β 1-4 | 20% | 3000 |
| Nigerose | glucose-glucose | β 1-3 | 80% | 1000 |
| Laminaritriose | glucose-glucose-glucose | β 1-3 | 20% | 2000 |
| Laminaritetraose | (glucose)4 | β 1-3 | 10% | 2500 |
| Laminaripentaose | (glucose)5 | β 1-3 | 5% | 3000 |

The same tests, applied to monosaccharides of the group comprising galactose, mannose and fucose, have shown that the activity of these products does not exceed 5% and that their optimal concentration is of the order of 3000 µg/ml.

In view of the results shown in table A, laminaribiose and nigerose are particularly preferred.

The control test in water leads to no activity; the control test with ;the germination buffer leads to an activity of 5% and an optimal concentration of 3500 µg/ml.

The fact that the optimal concentrations mentioned in the above table are close to the lower limit of the concentration ranges proposed above, is not surprising taking into account the very specific conditions used for laboratory experiments.

The invention is all the more surprising and unexpected insofar as no activity has been found for products of structures close to the selected products, i.e.:

maltose (glucose-glucose, α 1-4)

maltotriose (glucose-glucose-glucose, α 1-4)

α-trehalose (glucose-glucose, α 1-1)

β-trehalose (glucose-glucose, β 1-1)

sophorose (glucose-glucose, β 1-2)
galactobiose (galactose-galactose, β 1-6)
turanose (glucose-fructose, α 1-3)
maltitol (glucose-sorbitol, α 1-4)
raffinose (galactose-glucose-fructose, α 1-6, α 1-2).

Optimal concentrations of laminaribiose have also been determined for the stimulation of pollen grains
of lily,
of apple trees and
of cherry trees.

To do this, laminaribiose was used in the form of a sprayable composition, of 80% by weight and purity responding to the above conditions.

This composition was tested after dilution in water at concentrations from 1 μg/ml to 300 μg/ml.

An activity of 80% was found for concentrations of laminaribiose of 100 to 300 μg/ml in the case of lily, for concentrations of 200 to 300 μg/ml in the case of apple trees and an activity of 50% for concentrations of 50 to 300 μg/ml in the case of cherry trees.

The stimulation of the germination of pollen grains by the phytosanitary products used in the process and the compositions according to the invention was confirmed by field tests.

EXAMPLE 8

Treatment of Corn in the Field

This experiment in the field consisted in treating a corn crop by application of a composition formulated at 80% by weight of laminaribiose constituted as follows:

| | |
|---|---|
| laminaribiose | 80% |
| moisture | 5% |
| inorganic matter | 10% |
| mannitol | 5% |
| | 100% |

This composition is in the form of a water soluble powder.

For application to corn plants, aqueous solutions were prepared starting from the above sprayable composition, at concentrations allowing the application of doses of laminaribiose per hectare from 2.5 to 100 g.

These solutions were applied on two strains A and B of corn of different qualities; strain A produced little pollen whereas strain B produced pollen in large quantities.

For each of the two strains A and B, the experiment was conducted on a parcel containing two times eight rows of corn plants. Each mode of treatment was composed of a row of 20 male plants and a row of 20 female plants, the two rows being side by side.

The first two rows which constituted the first mode of treatment, were the control rows.

The pairs of rows of modes of treatment 2 to 4 were treated with the above composition respectively at doses of laminaribiose of 2.5 g/ha, 5 g/ha and 10 g/ha.

The fifth mode of treatment again comprised two control rows.

The pairs of rows of modes of treatment 6 to 8 were treated respectively with the above composition at doses of laminaribiose of 50 g/ha, 75 g/ha and 100 g/ha.

In each case, the percentage G of germinated grains was noted.

The experiment was performed at different stages of flowering.

The best results were recorded in performing the application upon opening of the anthers.

BRIEF DESCRIPTION OF THE DRAWINGS

These latest results, obtained with the strains A and B, were plotted on two histograms I and II respectively represented in FIGS. 1 and 2 and showing the percentage G of germinated grains as a function of the dose L (in g/ha) of laminaribiose.

An examination of histograms I and II, shows that activity greater than 40% in the case of strain A and greater than 35% in the case of strain B are obtained for doses of laminaribiose of 50 g/ha to 100 g/ha.

EXAMPLE 9

Figure 1:
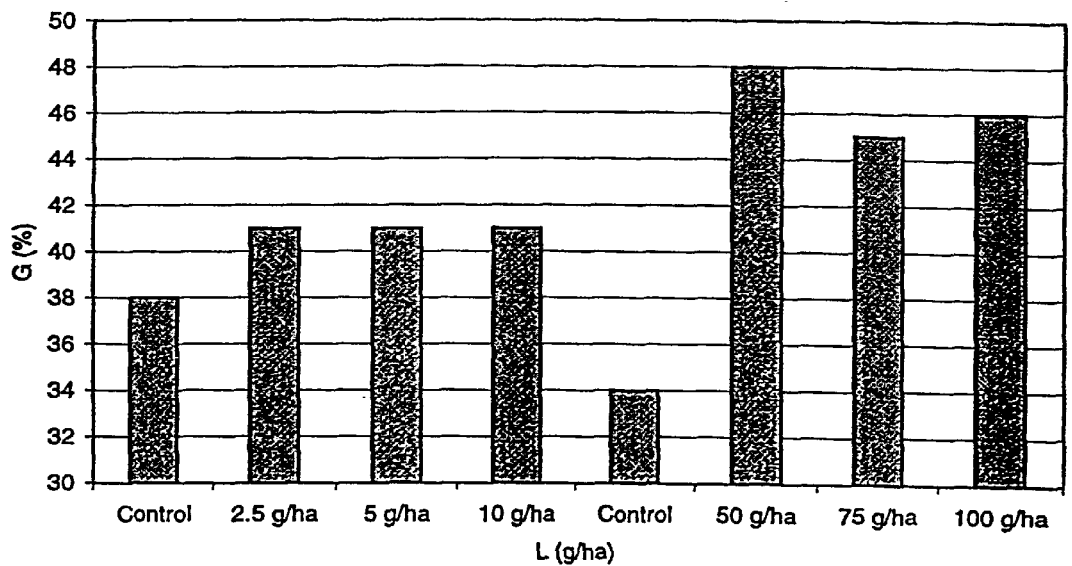
Figure 2:
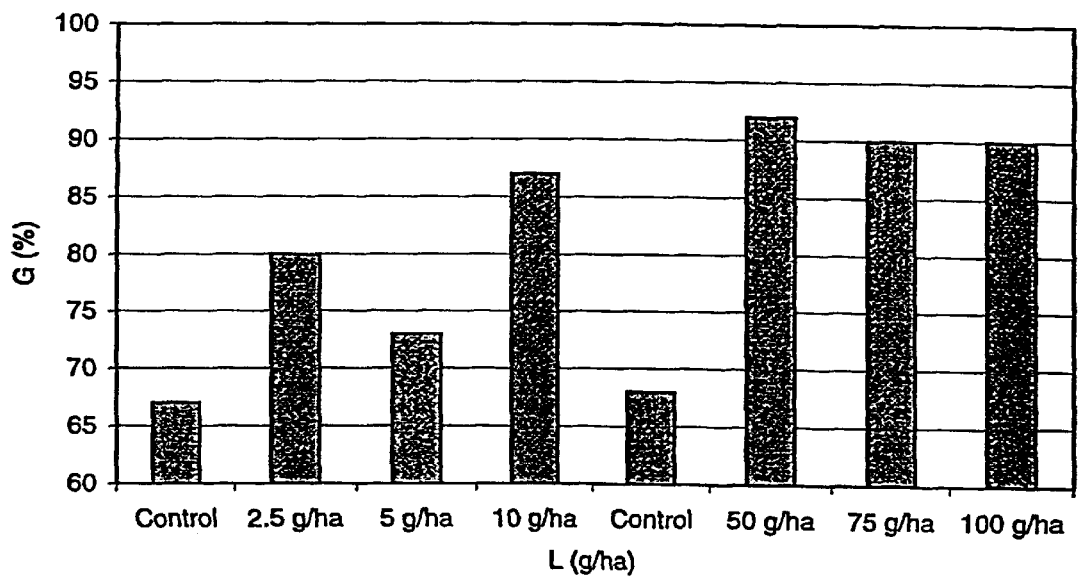

Treatment of a Variety of a Plum Tree in the Field

This experiment in the filed consisted in treating an orchard of Ente plum trees (clone P2733) of 15 years of age.

A composition at 65% by weight of laminaribiose constituted as follows was used:

| | |
|---|---|
| laminaribiose | 65% |
| moisture | 7% |
| inorganic matter | 15% |
| mannitol | 13% |
| | 100% |

This composition is in the form of a water soluble powder.

For application on plum trees, a solution in water of this composition was prepared at a concentration allowing administration of 65 g of laminaribiose per hectare.

A control parcel was treated with pure water.

The application was performed during full flowering.

Twigs were removed from representative plum trees in full flower on the treated and control parcels.

The anthers were recovered, by scraping, in a Petri dish which was placed in a dessicator for 24 hours to activate their dehiscence. Once the anthers were "ripe ", the pollen was put into test and placed in a refrigerator.

The rate of germination of the pollen was verified after seeding on gelosed medium (1% gelose and 15% saccharose). The pollen seeding was performed using a dry brush.

Two groups of 10 Petri dishes were seeded respectively with pollen from the control parcel and treated parcel.

The Petri dishes were then incubated at 22–23° C. and the observations, i.e. the counting, were performed 24 hours after seeding.

The observations are performed using a binocular magnifying glass.

10 observations of 20 pollen grains (corresponding to the field of the binocular magnifying glass) were performed per Petri dish; 2000 grains were thus observed for the treated parcel and 2000 for the control parcel.

During the 100 observations performed with respect to the 10 Petri dishes concerning the control parcel, on the one hand, and the 100 observation performed with the 10 Petri dishes concerning the treated parcel, on the other hand, were counted:

the non germinated grains,
the skeletons of pollen tubes,
pollen tubes of a length equal to 1 to 3 times the diameter of the pollen grains,
pollen tubes of a length greater than 1 to 3 times the diameter of the pollen grains,
the percentage of germinated grains.

In table B, below, the results of these observations as well as the percentages of variation between the results obtained for the control parcel and those for the parcel treated with the composition are shown; these percentages of variation indicate the effects of the treatment.

TABLE B

| 24 hours after seeding (gelosed medium) | Pollen from the control parcel | Pollen from the treated parcel | Effect of treatment (in %) |
|---|---|---|---|
| Non germinated grains | 1627 | 1264 | −22.3 |
| Skeletons of pollen tubes | 6 | 9 | +50 |
| Pollen tubes of length = 1 to 3 times the diameter of the pollen grains | 139 | 216 | +55.3 |
| Pollen tubes of length > 3 times the diameter of the pollen grains | 211 | 479 | +127 |
| % de germinated grains | 17.8 | 35.2 | +97.7 |

What is claimed is:

1. A method for stimulating germination of pollen grains comprising application to leaves of a plant of a composition comprising an excipient and an active ingredient capable of stimulating germination of pollen grains, wherein the active ingredient is selected from the group consisting of laminaribiose, nigerose, cellobiose, laminaritriose and combinations thereof.

2. The method of claim 1, wherein the composition further comprises a fungicide.

3. The method of claim 1, wherein the excipient is selected from the group consisting of water, mineral oils, vegetable oils, liquid fats and alcohol.

4. The method of claim 1, wherein the composition further comprises a component selected from the group consisting of a bulking agent, a solvent, a surface-active agent, a dispersing agent, an emulsifying agent and combinations thereof.

5. The method of claim 1, wherein the active ingredient is present in the composition in an amount of from about 1 to 20% by weight.

6. The method of claim 1, wherein the active ingredient is present in the composition in an amount of from about 1.5 to 10% by weight.

7. The method of claim 1, wherein the active ingredient is present in the composition in an amount of from about 2 to 8% by weight.

8. The method of claim 1, wherein the composition is applied in an amount of from about 10 to 1000 g of active ingredient per hectare.

9. The method of claim 1, wherein the composition is applied in an amount of from about 20 to 500 g of active ingredient per hectare.

10. The method of claim 1, wherein the composition is applied in an amount of from about 50 to 250 g of active ingredient per hectare.

11. The method of claim 1, wherein the composition is applied to the leaves by spraying, and wherein the spraying occurs at one or more of the following times, during flowering, during pollenization, before opening of anthers, or during opening of anthers.

* * * * *